(12) United States Patent
Wu et al.

(10) Patent No.: US 8,515,156 B2
(45) Date of Patent: Aug. 20, 2013

(54) IMAGE ANALYSIS DEVICE AND METHOD

(75) Inventors: Wen-Wu Wu, Shenzhen (CN);
Meng-Zhou Liu, Shenzhen (CN);
Xiao-Jun Fu, Shenzhen (CN)

(73) Assignees: Hong Fu Jin Precision Industry (ShenZhen) Co., Ltd., Shenzhen (CN);
Hon Hai Precision Industry Co., Ltd., New Taipei (TW)

( * ) Notice: Subject to any disclaimer, the term of this patent is extended or adjusted under 35 U.S.C. 154(b) by 151 days.

(21) Appl. No.: 13/211,320

(22) Filed: Aug. 17, 2011

(65) Prior Publication Data
US 2012/0141010 A1 Jun. 7, 2012

(30) Foreign Application Priority Data
Dec. 1, 2010 (CN) .......................... 2010 1 0568561

(51) Int. Cl.
*G06K 9/62* (2006.01)
(52) U.S. Cl.
USPC ........................................................ 382/149

(58) Field of Classification Search
None
See application file for complete search history.

(56) References Cited

U.S. PATENT DOCUMENTS
5,495,535 A * 2/1996 Smilansky et al. ........... 382/145

* cited by examiner

*Primary Examiner* — Brian P Werner
(74) *Attorney, Agent, or Firm* — Altis Law Group, Inc.

(57) ABSTRACT

An image analysis device reads a reference image and a real-time image of a printed circuit board (PCB), determines feature points and feature information of the feature points in the reference image; and creates two 1×N matrices based on the feature points. Furthermore, a mapping matrix is determined based on the two 1×N matrices. The device then reads coordinates of base points designated in the reference image, and determines matching points in the real-time image based on the coordinates of base points and the mapping matrix. A reference region in the reference image is determined based on all the base points, and a matching region is determined in the real-time image based on all the matching points. The reference region and the matching region are compared to determine existence of any surface feature defects of the PCB.

18 Claims, 5 Drawing Sheets

IMAGE ANALYSIS DEVICE AND METHOD

BACKGROUND

1. Technical Field

Embodiments of the present disclosure relate to data processing systems and methods, and more particularly, to an image analysis device and method.

2. Description of Related Art

Automated optical inspection (AOI) applies to a wide range of products, such as printed circuit boards (PCBs). In the case of PCB inspection, a self-directed camera scans a PCB under test to obtain a real-time image of the PCB. An inspection region of the PCB is designated in a reference image arising from the PCB design. Then, a matching region of the inspection region is determined in the real-time image, and the matching region is compared with the inspection region, to determine a variety of surface feature defects, such as scratches and stains, open circuits, short circuits, missing components, incorrect components, and incorrectly placed components. At present, the determination of the matching region is based on pixel information from the reference image and from the real-time image. However, in the PCB inspection, a camera may acquire data concerning millions of pixels from a small part of the PCB in one second. Therefore, determining the matching region based on pixel information involves a large number of calculations, which is time-consuming.

DETAILED DESCRIPTION

The disclosure, including the accompanying drawings in which like references indicate similar elements, is illustrated by way of examples and not by way of limitation. It should be noted that references to "an" or "one" embodiment in this disclosure are not necessarily to the same embodiment, and such references mean at least one.

In general, the word "module", as used herein, refers to logic embodied in hardware or firmware, or to a collection of software instructions, written in a programming language, such as, Java, C, or assembly. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable media include CDs, DVDs, BLU-RAY, flash memory, and hard disk drives.

Figure 1:
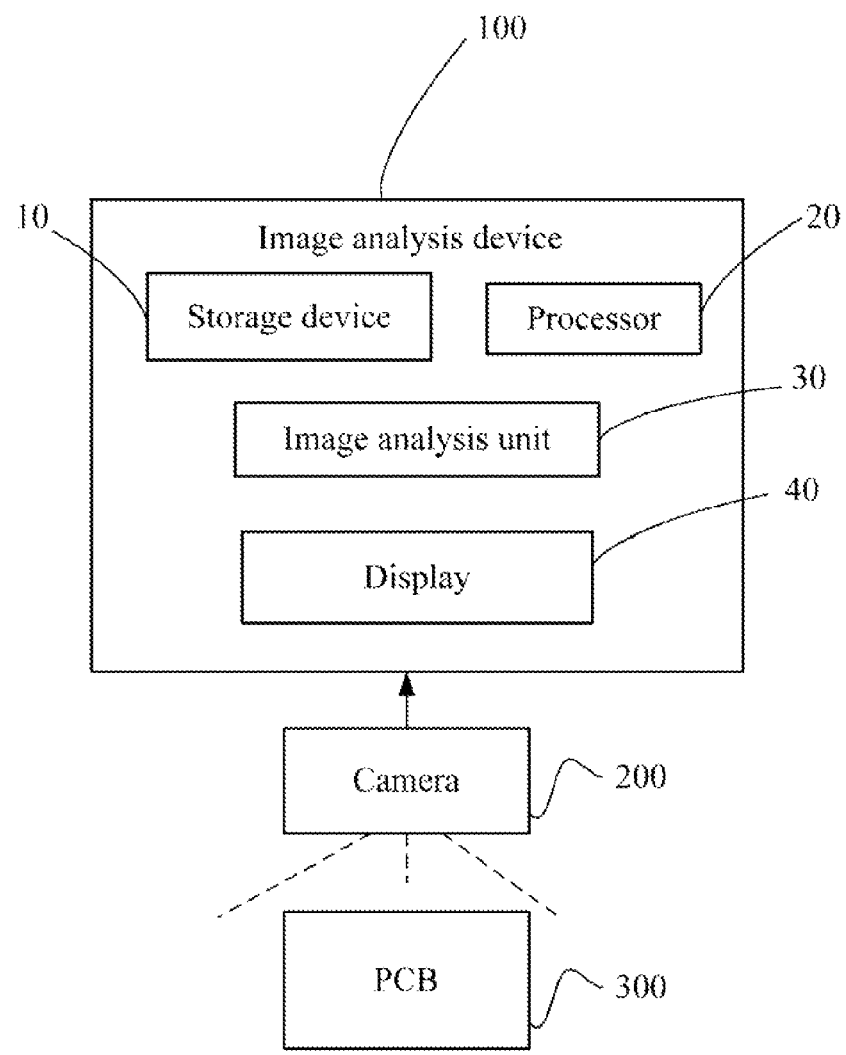
FIG. 1 is a block diagram of one embodiment of function modules of an image analysis device.

FIG. 1 is a block diagram of one embodiment of function modules of an image analysis device 100. Depending on the embodiment, the image analysis device 100 may be a computer, a server, or any other data processing device. The image analysis device 100 is connected to a camera 200. The camera 200 captures real-time images of one or more printed circuit boards (PCB) 300 (only one shown), and sends the real-time images to the image analysis device 100.

In one embodiment, the image analysis device 100 includes a storage device 10, a processor 20, an image analysis unit 30, and a display 40. The storage device 10 stores reference images of the PCBs 300 arising or gathered from designs of the PCBs 300, and stores the real-time images of the PCBs 300 that are captured by the camera 200. The image analysis unit 30 reads a reference image and a real-time image of a PCB 300, determines a reference region in the reference image, searches for the matching region of the reference region in a real-time image of the PCB 300, and compares the matching region and the reference region to determine surface feature defects of the PCB 300. The display 40 displays the reference images and the real-time images, and displays comparison results, such as marking or displaying a position of any surface feature defects of the PCB 300 in the real-time image.

Figure 2:
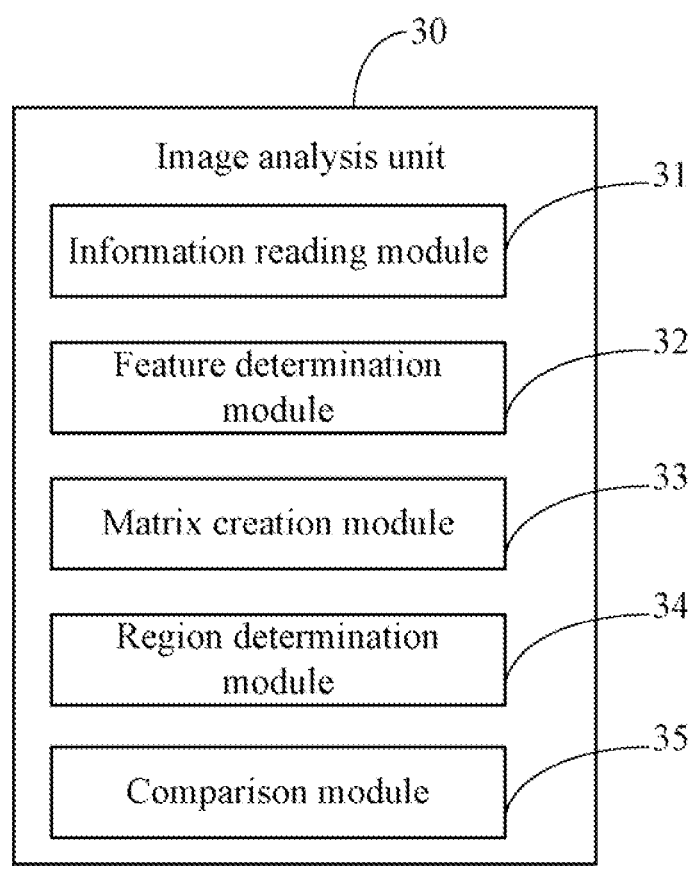
FIG. 2 is a block diagram of one embodiment of function modules of an image analysis unit in FIG. 1.

As shown in FIG. 2, the image analysis unit 30 includes an information reading module 31, a feature determination module 32, a matrix creation module 33, a region determination module 34, and a comparison module 35. The modules 31-35 may comprise computerized code in the form of one or more programs that are stored in the storage device 10. The computerized code includes instructions that are executed by the processor 20, to provide below mentioned functions of the modules 31-35 illustrated in FIG. 3.

Figure 3:
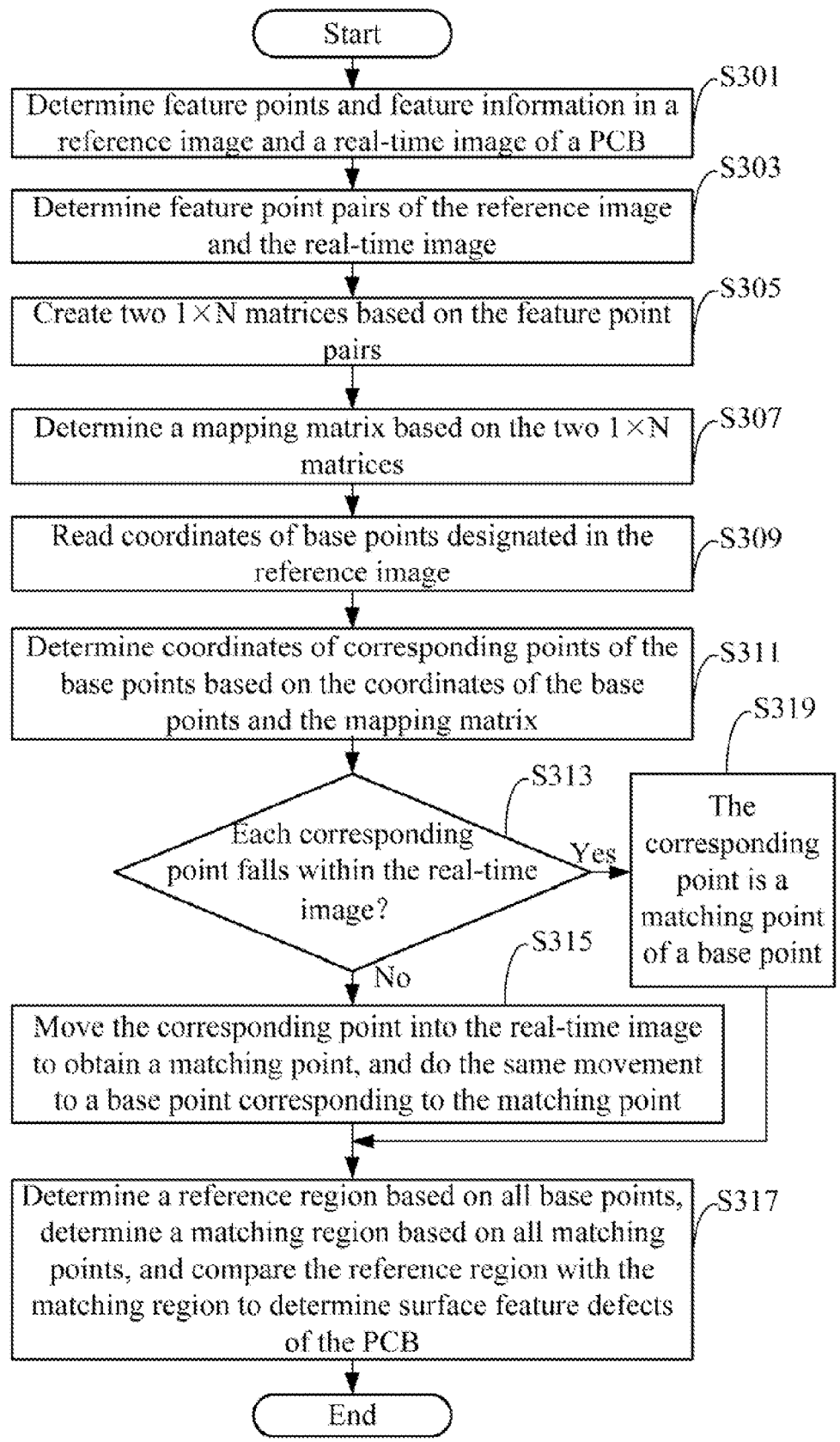
FIG. 3 is a block diagram of one embodiment of an image analysis method.

FIG. 3 is a flowchart of one embodiment of an image analysis method. Depending on the embodiment, additional blocks may be added, others removed, and the ordering of the blocks may be changed.

In block S301, the information reading module 31 reads a reference image and a real-time image of a PCB 300 from the storage device 10. The feature determination module 32 determines the feature points in the reference image and in the real-time image, and determines the feature information of the feature points using a mathematical algorithm. In one embodiment, the reference image and the real-time image are two-dimensional images. The mathematical algorithm can be the speeded up robust features (SURF) algorithm, in one example. A feature point is a pixel having an eigenvalue that is greater than a predetermined eigenvalue. The feature information of a feature point may include a direction, a scale, and a feature vector of the feature point. In another embodiment, the mathematical algorithm may be a scale-invariant feature transform (SIFT) algorithm.

In block S303, the feature determination module 32 determines feature point pairs of the reference image and the real-time image based on the feature information of the feature points. It is understood that, a feature point pair consists of a feature point (e.g., P4 shown in FIG. 4) in the reference image and a corresponding feature point (e.g., P8 shown in FIG. 5) in the real-time image. In this embodiment, the feature determination module 32 determines similarity of the feature points in the reference image and the real-time image according to Euclidean distances of the feature vectors of the feature points. For example, the feature determination module 32 reads a feature point A1 from the reference image, and searches out two feature points B1 and B2 in the real-time image, based on the feature point B1 having the nearest Euclidean distance D1 to the feature point A1, and the feature point B2 having the next nearest Euclidean distance D2 to the feature point A1. If a ratio of the nearest Euclidean distance D1 to the next nearest Euclidean distance D2 is less than a predetermined value (e.g., 0.8), the feature determination module 32 determines that the feature point A1 and the feature point B1 are a feature point pair.

In block S305, the matrix creation module 33 creates two 1×N matrices based on the feature point pairs. For example, supposing there are N feature point pairs such as (A1, B1), (A2, B2), (A3, B3), ..., (AN, BN), where A1-AN are feature points in the reference image, and B1-Bn are feature points in the real-time image. Then, the matrix creation module 33 creates a first 1×N matrix A1=[A1, A2, A3, ..., AN], and a second 1×N matrix B=[B1, B2, B3, ..., BN].

In block S307, the matrix creation module 33 determines a mapping matrix based on the two 1×N matrices. For example, the matrix creation module 33 determines a mapping matrix E based on a formula A×E=B.

Figure 4:
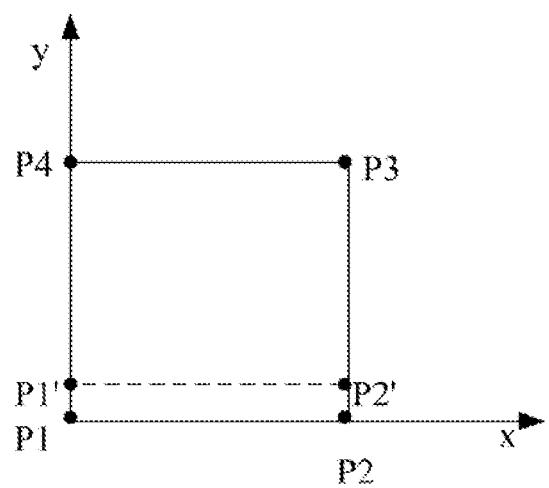
FIG. 4 illustrates an example of base points in a reference image of a PCB.

In block S309, the information reading module 31 reads coordinates of all base points designated in the reference image. The base points are used to define a reference region in the reference image, and may be selected from the feature points in the reference image, or from any other suitable pixels in the reference image. In one embodiment, as shown in FIG. 4, four base points P1 (0, 0), P2 (w, 0), P3 (w, h), P4 (0, h) are designated, where w>0, h>0. The base point P1 (0, 0) is an origin of a two-dimensional coordinate system, where w represents a width of the reference image, and h represents a height of the reference image.

Figure 5:
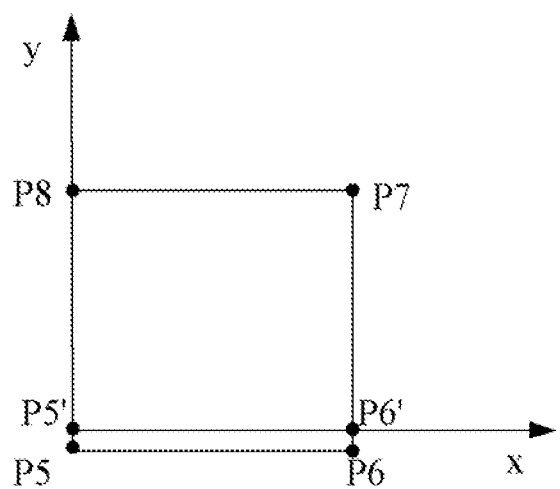
FIG. 5 illustrates an example of matching base points in a real-time image of the PCB.

In block S311, the region determination module 34 determines coordinates of corresponding points of the base points in the real-time image based on the coordinates of the base points and the mapping matrix. For example, if the corresponding points of the base points P1, P2, P3, and P4 are P5, P6, P7, and P8 (as shown in FIG. 5), then P1×E=P5, P2×E=P6, P3×E=P7, and P4×E=P8.

In block S313, the region determination module 34 determines if any corresponding point is found within the real-time image. If the corresponding point is found within the real-time image, block S319 is implemented, as the region determination module 34 determines that the corresponding point is a matching point of a base point. Then, the procedure goes to block S317. It should be noted that, in one situation, the mapping matrix may include negatives, and as a result, the X, Y coordinate values of a corresponding point may include negatives, which represent the corresponding point outside the real-time image. In another situation, if the X coordinate value is greater than the width of the reference image, or if the Y coordinate value is greater than then height of the reference image, the corresponding point is determined to be outside the real-time image. If the corresponding point falls outside of the real-time image, block S315 is implemented.

In block S315, the region determination module 34 moves the corresponding point into the real-time image to obtain a matching point, and does the same movement to a base point corresponding to the matching point. For example, as shown in FIG. 4 and FIG. 5, if the coordinates of the four base points P1-P4 are respectively P1(0, 0), P2(400, 0), P3(400, 312), P4(0, 312), the coordinates of the corresponding points P5-P8 of the base points P1-P4 are respectively P5(0, −4), P6(400, −4), P7(399, 308), P8(0, 308), and in that case the corresponding points P5 and P6 are determined to fall outside of the real-time image. The region determination module 34 moves the corresponding points P5 and P6 along the positive direction of the y-axis by four units (e.g., by four millimeters) in the two-dimensional coordinates, to obtain the matching points P5'(0, 0) and P6'(400, 0). Furthermore, the region determination module 34 moves the base points P1(0, 0), P2(400, 0), which match the matching points P5'(0, 0) and P6'(400, 0), along the positive direction of the y-axis by the same four units (e.g., by four millimeters) in the two-dimensional coordinates, to obtain two new base points P1'(0, 4), P2'(400, 4).

In block S317, the region determination module 34 determines a reference region based on all base points, and determines a matching region based on all matching points. For example, as shown in FIG. 4 and FIG. 5, the reference region is defined by the base points P1'(0, 4), P2'(400, 4), P3(400, 312), P4(0, 312), and the matching region is defined by the matching points P5'(0, 0), P6'(400, 0), P7(399, 308), and P8(0, 308). The comparison module 35 then compares the reference region with the matching region to determine any surface feature defects of the PCB 300.

Although certain embodiments of the present disclosure have been specifically described, the present disclosure is not to be construed as limited thereto. Various changes or modifications may be made to the present disclosure without departing from the scope and spirit of the present disclosure.

What is claimed is:

1. A computer-implemented image analysis method being executed by a processor of a computing device, comprising:
    reading a reference image of a printed circuit board (PCB) from a design of the PCB stored in a storage device by the processor, and reading a real-time image of the PCB captured by a camera and stored in the storage device by the processor;
    determining feature points and feature information of the feature points in the reference image using a mathematical algorithm by the processor;
    determining feature point pairs of the reference image and the real-time image based on the feature information of the feature points by the processor, wherein a feature point pair consists of a feature point in the reference image and a corresponding feature point in the real-time image;
    creating two 1×N matrices based on the feature point pairs, and determining a mapping matrix based on the two 1×N matrices by the processor;
    reading coordinates of base points designated in the reference image by the processor;
    determining matching points in the real-time image based on the coordinates of the base points and the mapping matrix by the processor;
    determining a reference region in the reference image based on all the base points, and determining a matching region in the real-time image based on all the matching points by the processor; and
    comparing the reference region with the matching region to determine surface feature defects of the PCB by the processor.

2. The method of claim 1, wherein determining matching points comprises:
    determining coordinates of corresponding points of the base points based on the coordinates of the base points and the mapping matrix;
    determining a corresponding point is a matching point if the corresponding point falls within the real-time image; and
    moving a corresponding point into the real-time image to obtain a matching point if the corresponding point falls out of the real-time image, and doing the same movement to a base point corresponding to the matching point in the reference image.

3. The method of claim 1, wherein a feature point is a pixel having an eigenvalue greater than a predetermined eigenvalue.

4. The method of claim 1, wherein the feature information of a feature point comprises a direction, a scale, and a feature vector of the feature point.

5. The method of claim 2, wherein the corresponding point is determined to fall outside of the real-time image on condition that coordinate values of the corresponding point comprise negatives, or an X coordinate value of the corresponding point is greater than a width of the reference image, or a Y coordinate value of the corresponding point is greater than a height of the reference image.

6. The method of claim 4, wherein the feature point pairs are determined according to similarity between the feature points in the reference image and the real-time image, and the similarity of the feature points in the reference image and the real-time image are determined according to Euclidean distances of the feature vectors of the feature points.

7. A non-transitory computer readable medium storing a set of instructions, the set of instructions capable of being executed by processors to perform an image analysis method, the method comprising:
- reading a reference image of a printed circuit board (PCB) from a design of the PCB, and reading a real-time image of the PCB captured by a camera;
- determining feature points and feature information of the feature points in the reference image using a mathematical algorithm;
- determining feature point pairs of the reference image and the real-time image based on the feature information of the feature points, wherein a feature point pair consists of a feature point in the reference image and a corresponding feature point in the real-time image;
- creating two 1×N matrices based on the feature point pairs, and determining a mapping matrix based on the two 1×N matrices;
- reading coordinates of base points designated in the reference image;
- determining matching points in the real-time image based on the coordinates of the base points and the mapping matrix;
- determining a reference region in the reference image based on all the base points, and determining a matching region in the real-time image based on all the matching points; and
- comparing the reference region with the matching region to determine surface feature defects of the PCB.

8. The non-transitory computer readable medium of claim 7, wherein determining matching points comprises:
- determining coordinates of corresponding points of the base points based on the coordinates of the base points and the mapping matrix;
- determining a corresponding point is a matching point if the corresponding point falls within the real-time image; and
- moving a corresponding point into the real-time image to obtain a matching point if the corresponding point falls out of the real-time image, and doing the same movement to a base point corresponding to the matching point in the reference image.

9. The non-transitory computer readable medium of claim 7, wherein a feature point is a pixel having an eigenvalue greater than a predetermined eigenvalue.

10. The non-transitory computer readable medium of claim 7, wherein the feature information of a feature point comprises a direction, a scale, and a feature vector of the feature point.

11. The non-transitory computer readable medium of claim 8, wherein the corresponding point is determined to fall outside of the real-time image on condition that coordinate values of the corresponding point comprise negatives, or an X coordinate value of the corresponding point is greater than a width of the reference image, or a Y coordinate value of the corresponding point is greater than then a height of the reference image.

12. The non-transitory computer readable medium of claim 10, wherein the feature point pairs are determined according to similarity between the feature points in the reference image and the real-time image, and the similarity of the feature points in the reference image and the real-time image are determined according to Euclidean distances of the feature vectors of the feature points.

13. An image analysis device, comprising:
- a storage device;
- a processor; and
- one or more programs stored in the storage device and executable by the processor, the one or more programs comprising:
  - an information reading module operable to read a reference image of a printed circuit board (PCB) from a design of the PCB, and read a real-time image of the PCB captured by a camera;
  - a feature determination module operable to determine feature points and feature information of the feature points in the reference image, and determine feature point pairs of the reference image and the real-time image based on the feature information of the feature points, wherein a feature point pair consists of a feature point in the reference image and a corresponding feature point in the real-time image;
  - a matrix creation module operable to create two 1×N matrices based on the feature point pairs, and determining a mapping matrix based on the two 1×N matrices;
  - a region determination module operable to determine matching points in the real-time image based on coordinates of base points designated in the reference image and the mapping matrix, determine a reference region in the reference image based on all the base points, and determine a matching region in the real-time image based on all the matching points; and
  - a comparison module operable to compare the reference region with the matching region to determine surface feature defects of the PCB.

14. The device of claim 13, wherein determining matching points comprises:
- determining coordinates of corresponding points of the base points based on the coordinates of the base points and the mapping matrix;
- determining a corresponding point is a matching point if the corresponding point falls within the real-time image; and
- moving a corresponding point into the real-time image to obtain a matching point if the corresponding point falls out of the real-time image, and doing the same movement to a base point corresponding to the matching point in the reference image.

15. The device of claim 13, wherein a feature point is a pixel having an eigenvalue greater than a predetermined eigenvalue.

16. The device of claim 13, wherein the feature information of a feature point comprises a direction, a scale, and a feature vector of the feature point.

17. The device of claim 14, wherein the corresponding point is determined to fall outside of the real-time image on condition that coordinate values of the corresponding point comprise negatives, or an X coordinate value of the corresponding point is greater than a width of the reference image, or a Y coordinate value of the corresponding point is greater than then a height of the reference image.

18. The device of claim 16, wherein the feature point pairs are determined according to similarity between the feature points in the reference image and the real-time image, and the similarity of the feature points in the reference image and the real-time image are determined according to Euclidean distances of the feature vectors of the feature points.

* * * * *